United States Patent [19]

Endo et al.

[11] 4,191,574

[45] Mar. 4, 1980

[54] PROCESS FOR FORMING A PHOTOGRAPHIC MAGENTA DYE IMAGE

[75] Inventors: Takaya Endo; Shui Sato; Shoji Kikuchi; Tamotsu Kozima; Tugumoto Usui; Hiroyuki Imamura; Koichi Takabe, all of Hino, Japan

[73] Assignee: Konishiroku Photo Industry Co., Ltd., Tokyo, Japan

[21] Appl. No.: 930,315

[22] Filed: Aug. 2, 1978

Related U.S. Application Data

[63] Continuation of Ser. No. 659,025, Feb. 18, 1976, abandoned.

[30] Foreign Application Priority Data

Feb. 21, 1975 [JP] Japan .................................. 50/21607

[51] Int. Cl.$^2$ ........................... G03C 7/00; G03C 1/40

[52] U.S. Cl. .................................... 430/387; 430/555; 430/558

[58] Field of Search ....................... 96/56.5, 100, 56.2, 96/56.3, 56.4, 56.6

[56] References Cited

U.S. PATENT DOCUMENTS

| | | | |
|---|---|---|---|
| 3,311,476 | 3/1967 | Loria | 96/100 |
| 4,009,035 | 2/1977 | Kojima et al. | 96/100 |

*Primary Examiner*—Travis Brown
*Attorney, Agent, or Firm*—Bierman & Bierman

[57] ABSTRACT

A process for forming a photographic magenta dye image is disclosed which requires contacting exposed silver halide with a color developing agent in the presence of a particular class of 2-equivalent magenta couplers.

11 Claims, No Drawings

PROCESS FOR FORMING A PHOTOGRAPHIC MAGENTA DYE IMAGE

This is a Rule 60 Continuation application of Ser. No. 659,025 filed on Feb. 18, 1976, now abandoned which claims the priority of Japanese Patent Application No. 21607/1975 filed on Feb. 21, 1975.

The present invention relates to a process for forming a photographic image using a novel coupler, and particularly to a process for forming a photographic image using a novel magenta coupler.

In photographic technology, the use of silver halide as the photosensitive component for recording optical information is very common due to superior photographic properties thereof such as sensitivity or gradation. In such use of silver halide as the photosensitive component, there is commonly used a combination of silver halide and certain color developing compound in order to eventually obtain a colored image, said color developing compound being reacted with a certain reactive compound to form a dye in response to the information recorded by silver halide thereby constituting a dye image. Said color developing compound is called coupler and said reactive compound to be used in combination with said coupler for forming a dye is in general a color developer for example an aromatic primary amine color developer.

When a silver halide crystal having recorded light and thus have a developable nucleus therein is developed with a color developer in the presence of a coupler, said color developer reduces silver halide to form metallic silver and is simultaneously oxidized to form an active oxidation product which reacts with said coupler to form a dye, thereby resulting in the formation of a dye image corresponding to the information recorded by silver halide.

Said reaction between said coupler and said color developer takes place at the active position of coupler which is located in an active methyne or methylene radical in the coupler molecule.

A coupler provided with a hydrogen at such active position is called 4-equivalent coupler while that provided with a so-called split-off radical which is early liberated in the reaction with said color developer is called a 2-equivalent coupler.

Said 4-equivalent coupler requires 4-equivalents of silver halide with developable nucleus for reaction with color developer on an active position while a 2-equivalent coupler only requires 2-equivalents, so that the latter generally gives a dye image of a higher color density for a same amount of developed silver. Further, the 2-equivalent coupler is applicable for various purposes by suitably selecting the bonding radical which connects the split-off radical with the active position. For instance it is possible to provide the compound generated upon liberation of split-off radical with a development inhibiting effect, and, as an example of such case, a 2-equivalent coupler provided with a split-off radical with a thio (—S—) bonding radical is called a development inhibitor releasing (D.I.R.) coupler, which, being capable of suppressing the progress of development in proportion to the amount of developed silver, is applicable for various purposes. For example such D.I.R. coupler is capable of realizing so-called intra-image effects in a coupler-containing layer such as image tone control or finer granularity as well as so-called inter-image effects on other layers than said layer such as improvement in hue, and is further applicable to diffusion transfer process on account of said effect to other layers.

Certain 2-equivalent couplers such as those containing a dye portion in the split-off radical thereof are applicable to diffusion transfer process wherein the released dye is utilized for making an image of diffusible dye on an image receiving layer, and such coupler is called diffusible dye releasing (D.D.R.) coupler. Also certain colored 2-equivalent couplers are provided with a masking effect for color correction of a dye image and are called colored couplers.

The use of such 2-equivalent couplers has become common due to the inherent superiority thereof over 4-equivalent couplers and also the various applicability thereof.

On the other hand, however, the already known 2-equivalent couplers are associated with various disadvantages such as insufficient dye forming velocity, a tendency to cause fogging or stain in a photosensitive layer containing silver halide, or insufficient dispersion concentration attainable in the photosensitive layer.

The principal object of the present invention, therefore, is to provide a process for forming a photographic image using a novel 2-equivalent coupler which is free from the above mentioned drawbacks and which is further provided with excellent photographic properties.

An another object of the present invention is to provide a silver halide photographic sensitized material containing such novel 2-equivalent coupler.

More specifically, the present invention relates to a process for forming a photographic image using a 2-equivalent magenta coupler which comprises being provided at the active position thereof with at least one split-off radical with a 2-valent bonding radical of the following formula (I)

wherein R stands for a hydrogen atom or a monovalent organic radical and the carbonyloxy moeity of the formula (I) is bonded to an active position of a magenta coupler residue.

The above-mentioned 2-equivalent coupler to be employed in the present invention is provided at the active position thereof with a so-called urethane bond which gives rise to a faster dye forming speed, absence of fogging and stain in the photosensitive layer and satisfactory dispersibility in the constituent layers of photographic sensitized materials such as the photosensitive layer enabling a dispersion at an elevated concentration. Besides, the dye obtainable from said coupler exhibits an excellent resistance against light, heat and temperature and shows excellent sharp light absorption characteristics without unnecessary absorptions. Furthermore the 2-equivalent coupler of the present invention is not provided with the development inhibiting property which is found in certain 2-equivalent couplers.

The use of the 2-equivalent coupler of the present invention in a silver halide photographic sensitized material gives rise to various advantages such as possibility to obtain a thinner photosensitive layer, with resulting improved resolution and sharpness of color image, and, particularly in case of multi-layered photographic materials, an improved sensitivity due to elevated light transmission to the lower layers. The 2-equivalent couplers of the present invention comprises, as representative ones thereof, those represented by the following general formulas (II) and (III):

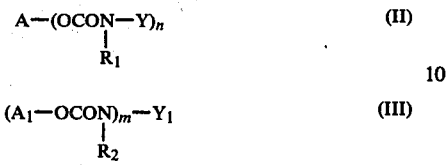

wherein A is an n-valent residue of magenta coupler, A₁ is a monovalent residue of magenta coupler, R₁ and R₂ have the same meaning as aforementioned R, Y is a monovalent organic radical, Y₁ is an m-valent organic radical, and n and m are positive integers.

The compounds of the above-mentioned general formulas (II) and (III) are representative basic couplers but 2-equivalent coupler wherein the structures of formulas (II) and (III) are mixedly present are also usable in the present invention. The magenta coupler residue in the above-mentioned general formulas (II) and (III) is a residue after the elimination of hydrogen atom or split-off radical on the active position thereof, and said residue may contain, if provided with plural active positions therein, same or different split-off radicals or may contain hydrogen atoms in a part of said active positions, but it is preferable that all the active positions in the molecule are provided with same split-off radicals of the present invention. The radical Y is preferably an aromatic hydrocarbon residue, an aliphatic hydrocarbon residue, a heterocyclic residue, an acyl radical, a thioclkyl radical or an —SO₂—X wherein X is an aliphatic hydrocarbon residue etc. and may contain substituents therein. The radical Y₁ is preferably an m-valent, aliphatic hydrocarbon residue, an aromatic hydrocarbon residue, a heterocyclic residue etc. which may contain substituents, or can further be an m-valent radical obtained by mutual combination of the above-mentioned radicals, for example a compound divalent radical obtained from a combination of divalent aliphatic hydrocarbon residues and arylene radicals wherein k members (k being a positive integer) selected from divalent aliphatic hydrocarbon residues and l members (l being a positive integer) selected from arylene radicals are mutually bonded in blocks or in random manner. Furthermore, said m-valent radicals may be provided with a carbonyl, thiocarbonyl or sulfonyl radical on the extremity thereof, and two neighboring carbon atoms therein may be intercepted by a carbon, oxygen or sulfur atom, an amino, sulfonyl, carbonyloxy, aminocarbonyl or sulfoamide radical. The radicals R, R₁ and R₂ are preferably a hydrogen atom, an acyl radical, an aliphatic hydrocarbon radical etc. The integers n and m are preferably 1 or 2, but may assume a value of 3 or even larger values when magnenta couplers known as polymer couplers are employed.

The preferred coupler residue, after elimination of the split-off radical, of the 2-equivalent magenta coupler of the present invention is represented by the following general formulas (IV) and (V):

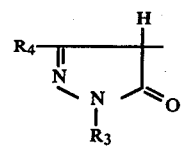

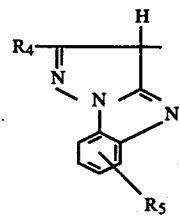

wherein R₃ and R₄ represent radicals employed in ordinary 4-equivalent pyrazolone couplers, and more specifically R₃ is a hydrogen atom or a radical containing 1 to approximately 50 carbon atoms preferably 1 to approximately 35 carbon atoms selected from normal or lamified alkyl radicals such as methyl, ethyl, isopropyl, t-butyl, hexyl, t-octyl or dodecyl radical; alkenyl radicals such as allyl radical; cycloalyl radicals such as cyclohexyl or norbonyl; and alkyl and cycloalkyl radicals provided with substituents selected from halogen atoms and nitro, cyano, aryl, alkoxy, aryloxycarboxy, alkoxycarbonyl, aryloxycarbonyl, sufo, sulfamoyl, carbamoyl, acylamino, ureid, heterocyclic, arylsulfonyloxy and oxo radicals, such as β-cyanoethyl, β-chloroethyl, benzyl, nitrobenzyl, dichlorobenzyl, γ-(2,4-di-t-amylphenoxy)-propyl or β-phenoxyethyl radical. Further R₃ can be an aryl radical such as phenyl, α- or β-naphthyl radical; or an aryl radical provided with at least a substituent radical selected from halogen atoms and alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro radicals. Particularly effective example of R₃ is a phenyl radical of which at least one of ortho positions is substituted with an alkyl or alkoxy radical or a halogen atom. Furthermore R₃ can be a heterocyclic radical containing 5-membered or 6-membered heterocyclic or condense heterocyclic radical with nitrogen, oxygen, sulfur atoms etc. as hetero atoms therein such as pyridyl, quinolyl, furyl, benzothiazolyl, oxazolyl, imidazolyl or naphthoxazolyl radical, or a heterocyclic radical provided with substituent radicals listed for above-mentioned aryl radical. Furthermore R₃ can also be a carbamoyl or thiocarbamoyl radical.

R₄ is a radical containing 1 to approximately 50 carbon atoms preferably 1 to approximately 35 carbon atoms selected from alkyl, substituted alkyl, aryl, substituted aryl, heterocyclic or substituted heterocyclic radicals same as those listed for R₃. Further R₄ can also be an alkoxycarbonyl radical such as methoxycarbonyl or ethoxycarbonyl radical; an aryloxycarbonyl radical; an aralyloxycarbonyl radical; a substituted oxy radical such as methoxy, ethoxy, phenoxy or tolyloxy radical; a substituted thio radical such as ethylthio, propylthio, phenylthio or tolylthio radical; a carboxy radical; an amino radical such as N-alkylamino, cycloalkylamino, N, N-dialkylamino, N-alkyl-N-arylamino or N-arylamino; an amido radical such as acetamido, α-(2,4-di-t-amylphenoxy)acetamido, α-butoxyphenoxypropionamido, α-(3-pentadecyl-4-sulfophenoxyacetamido)- benzamido, benzamido or benzenesulfonamido, radical; an N-alkylacylamino radical; an N-arylacylamino radical; an ureid radical such as N-arylureid or N-arkylureid radical; a thioureid radical such as N-alkylthioureid or N-arylthioureid radical; a carbamoyl radical such as N-octadecylcarbamoyl, 3-pentadecylphenylcarbamoyl or N-methyl-N-phenylcarbamoyl; a guanidino radical such as guanidino, N-alkylguanidino or N-arylguanidino radical; a sulfamoyl radical, a piperidino radical or a pyroridino radical.

$R_5$ is one to four monovalent radicals selected from a hydrogen atom, halogen atoms such as chlorine atom, alkyl radicals such as methyl or ethyl radical, alkoxy radicals such as methoxy or ethoxy radical, amido radicals such as acetamido, benzenesulfonamido or 2,4-di-t-amylphenoxyacetamido radical, carbamoyl radicals such as dodecylcarbamoyl radical, and sulfamoyl radicals such as dodecylsulfamoyl radical.

The aliphatic hydrocarbon residue to be employed as the radical Y or $Y_1$ in the foregoing general formulas (II) and (III) can be either saturated or unsaturated and straight-chained, lamified or cyclic, and can be exemplified, in case of a monovalent residue, by an alkyl or alkenyl radical preferably methyl, ethyl, isobutyl, octyl, t-octyl, octadecyl cyclobutyl, cyclohexyl or 2-norbonyl radical, or in case of a divalent residue, by an alkylene radical preferably methylene, ethylene, butylene or hexylene radical. Also the aromatic hydrocarbon residue can be exemplified by an aryl or arylene radical preferably phenyl, naphthyl, phenylene or naphthylene radical. The heterocyclic residue is preferably a residue of a 5- or 6-membered heterocycle containing nitrogen, oxygen, sulfur atoms etc. as hetero atoms which can be monovalent residue preferably thienyl, pyridinyl, quinolyl or oxadiazolyl or divalent residue preferably pyridinylene or quilinolene radical. The preferred example of acyl radical is acetyl, benzoyl or naphthoyl radical, and that of thioacyl radical is thioacetyl, thiobenzoyl or thionaphthoyl radical, and that of sulfonyl radical is phenylsulfonyl, chlorosulfonyl or methanesulfonyl radical.

Furthermore, the various radicals to be employed as the radicals Y, $R_1$, $Y_1$ and $R_2$ in the foregoing general formulas (II) and (III) or the radical R in the foregoing general formula (I) may be, as explained before, provided with substituents which can be exemplified by the substituents employed in the foregoing general formulas (IV) and (V).

In the following shown are the representative examples of split-off radical provided with a divalent bonding radical shown by the foregoing general formula (I) of which carbonyloxy part is placed at the active position side of the coupler residue:

Methylaminocarbonyloxy radical:

—OCONHCH₃

Ethylaminocarbonyloxy radical:

—OCONHC₂H₅

Butylaminocarbonyloxy radical:

—OCONHC₄H₉(iso, tert, sec)

Propylaminocarbonyloxy radical:

—OCONHC₃H₇(iso)

Dodecylaminocarbonyloxy radical:

—OCONHC₁₂H₂₅

Octadecylaminocarbonyloxy radical:

—OCONHC₁₈H₃₇

2,4-di-t-amylphenoxymethylaminocarbonyloxy radical:

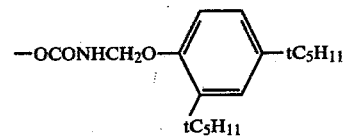

Phenethylaminocarbonyloxy radical:

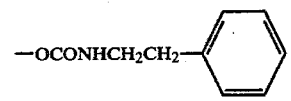

Benzylaminocarbonyloxy radical:

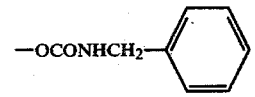

Anilinocarbonyloxy radical:

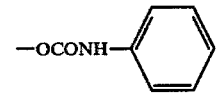

α-naphthylaminocarbonyloxy radical:

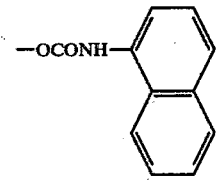

β-naphthylaminocarbonyloxy radical:

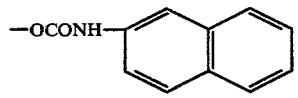

4-nitroanilinocarbonyloxy radical:

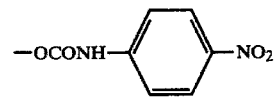

4-chloroanilinocarbonyloxy radical:

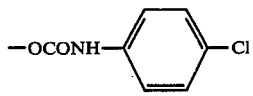

4-methylanilinocarbonyloxy radical:

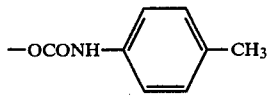

2,4-dimethylanilinocarbonyloxy radical:

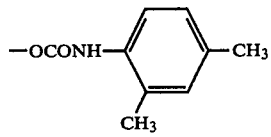

4-aminoanilinocarbonyloxy radical:

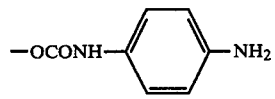

Ethylenebisaminocarbonyloxy radical:

—OCONH—CH₂CH₂—NHCOO—

Hexamethylenebisaminocarbonyloxy radical:

—OCONH—(CH₂CH₂)₃—NHCOO—

4,4′-methylenbisanilinocarbonyloxy radical:

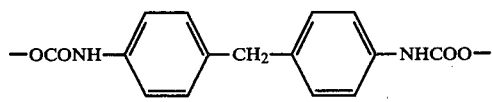

1,4-phenylenebisaminocarbonyloxy radical:

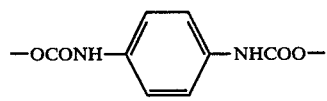

1,3-phenylenebisaminocarbonyloxy radical:

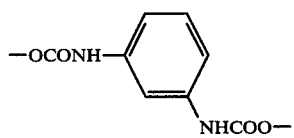

1,5-naphthalenebisaminocarbonyloxy radical:

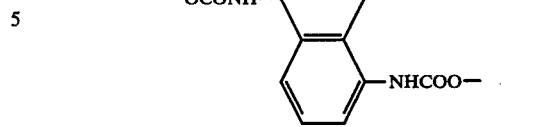

4,4′-diphenylenebisaminocarbonyloxy radical:

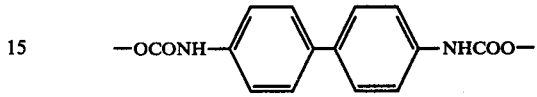

2,4-tolylenebisaminocarbonyloxy radical:

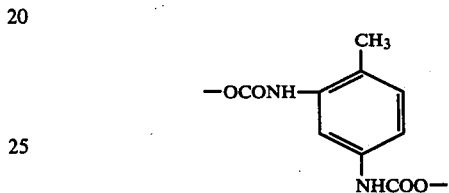

6-methoxy-4-quinolylaminocarbonyloxy radical:

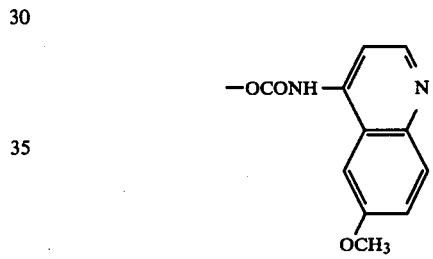

Benzoylaminocarbonyloxy radical:

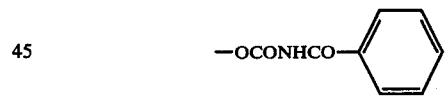

Chloroacetylaminocarbonyloxy radical:

—OCONHCOCH₂Cl

N-phenyl-N-acetylaminocarbonyloxy radical:

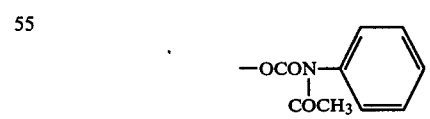

Phenylsulfonylaminocarbonyloxy radical:

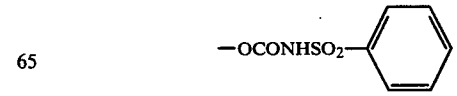

Thiobenzoylaminocarbonyloxy radical:

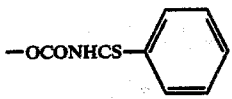

2,4-Tolylenebissulfonylaminocarbonyloxy radical:

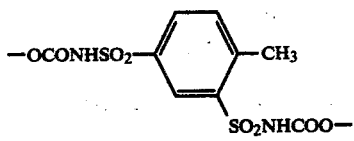

P-phenylenebiscarbonylaminocarbonyloxy radical:

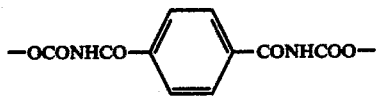

P-phenylenebisthiocarbonylaminocarbonyloxy radical:

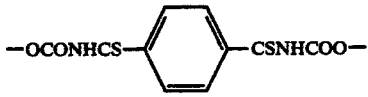

The couplers of the present invention are composed of the magenta coupler residues represented by the general formulas (IV) or (V) of which active positions are provided with the split-off radicals as explained in the foregoing, and the excellent photographic properties of such couplers are ascribed to the presence of aforementioned bonding radicals.

In the following there are shown representative examples of the couplers of the present invention, which however are by no means limited by these examples:

(1) 1-(2,4,6-trichlorophenyl)-3-[3-{α-(2,4-di-t-amylphenoxy)acetamido}benzamido]-4-anilinocarbonyloxy-5-pyrazolone

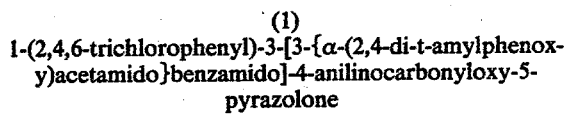

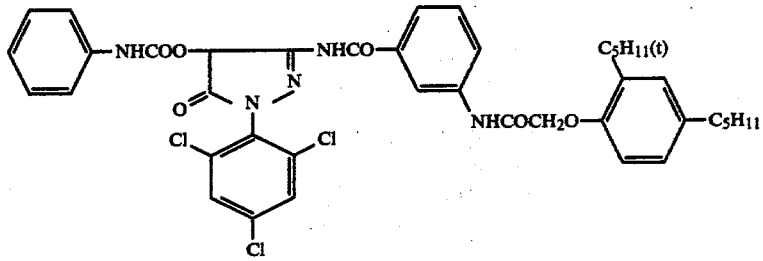

(2) 1-(2,4,6-trichlorophenyl)-3-[3-}α-(2,4-di-t-amylphenoxy)acetamidobenzamido}-4-(1-naphthylaminocarbonyloxy]-5-pyrazolone

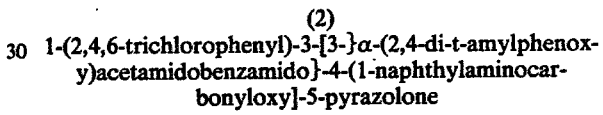

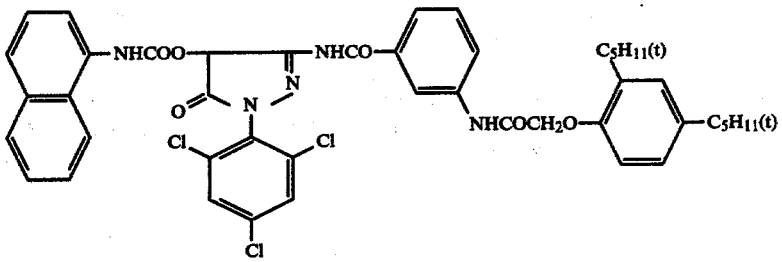

(3) 1-(2,4,6-trichlorphenyl)-3-[3-{α-(2,4-di-t-amylphenoxy)acetamido}benzamido]-4-(4-nitroanilinocarbonyloxy)-5-pyrazolone

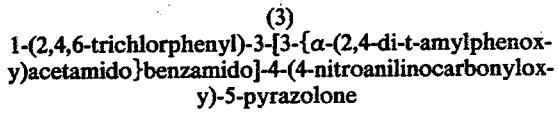

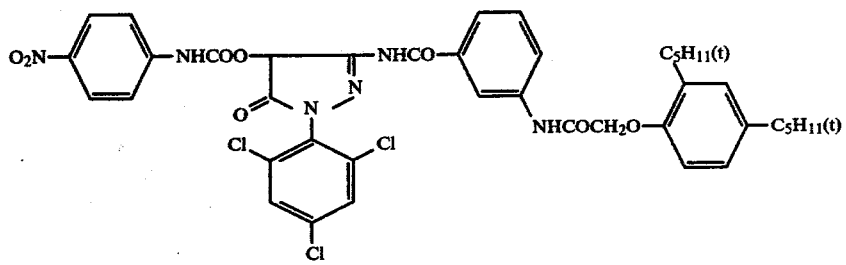

(4)
1-(2,4,6-trichlorophenyl)-3-[3-{α-(2,4-di-t-amylphenoxy)acetamido}benzamido]-4-(4-chloroanilinocarbonyloxy)-5-pyrazolone

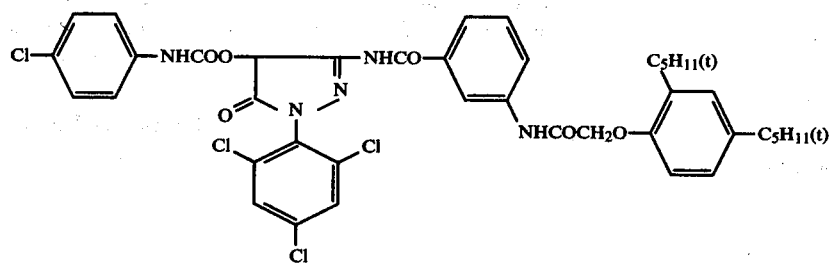

(5)
1-(2,4,6-trichlorphenyl)-3-[3-{α-(2,4-di-t-amylphenoxy)acetamido}benzamido]-4-(3-methylanilinocarbonyloxy)-5-pyrazolone

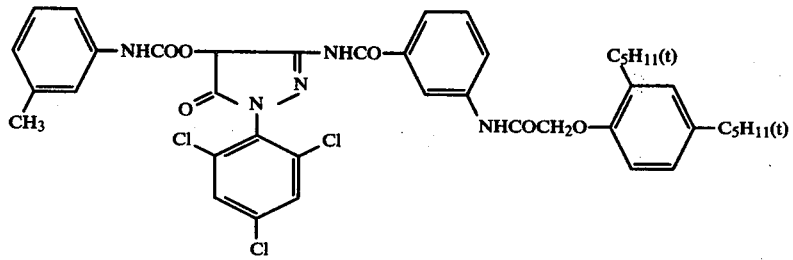

(6)
1-(2,4,6-trichlorphenyl)-3-[3-{α-(2,4-di-t-amylphenoxy)acetamido}benzamido]-4-benzylaminocarbonyloxy-5-pyrazolone

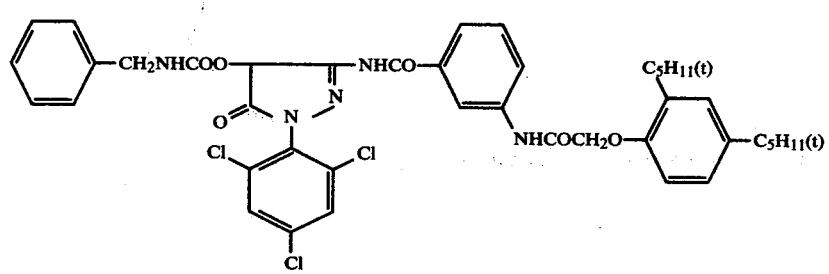

(7)
1-(2,4-dimethyl-6-chlorophenyl)-3-[4-{α-(3-pentadecylphenoxy)butanamido}benzamido]-4-ethylaminocarbonyloxy-5-pyrazolone

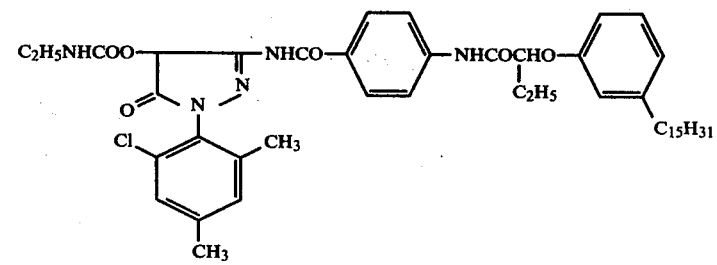

(8)
1-(2,4,6-trichlorophenyl)-3-[3-{α-(2,4-di-t-butylphenoxy)acetamido}benzamido]-4-benzoylaminocarbonyloxy-5-pyrazolone

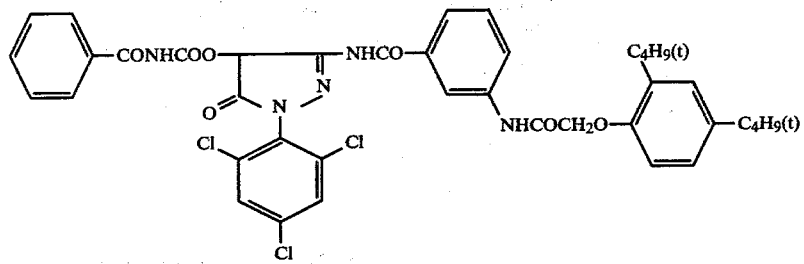

(9)
1-(2,4,6-trichlorophenyl)-3-{(2-chloro-4-n-hexadecanamido)anilino}-4-anilinocarbonyloxy-5-pyrazolone

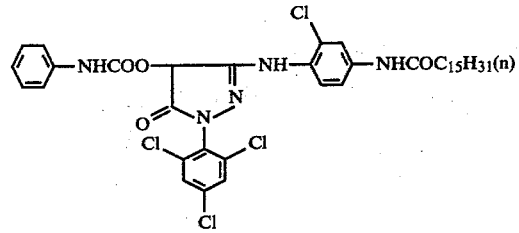

(10)
1-(2,4,6-trichlorophenyl)-3-{(2-chloro-4-n-hexadecanamido)anilino}-4-(α-naphthylaminocarbonyloxy)-5-pyrazolone

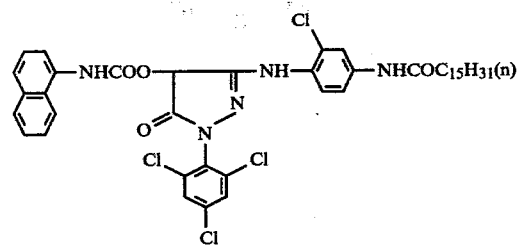

(11)
1-(2,4,6-trichlorophenyl)-3-{(2-chloro-4-n-hexadecanamido)anilino}-4-(4-nitroanilinocarbonyloxy)-5-pyrazolone

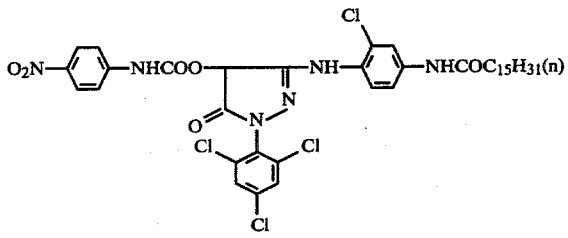

(12)
1-(2,4,6-trichlorophenyl)-3-{(2-chloro-4-n-hexadecanamido)anilino}-4-(4-chloroanilinocarbonyloxy)-5-pyrazolone

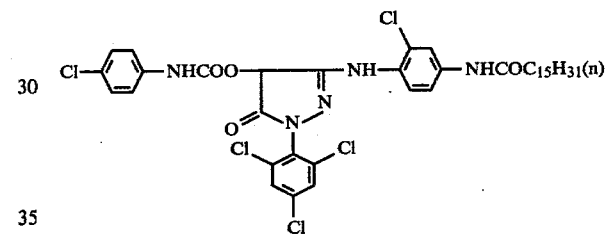

(13)
1-(2,4,6-trichlorophenyl)-3-{(2-chloro-4-n-hexadecanamido)anilino}-4-(3-toluylaminocarbonyloxy)-5-pyrazolone

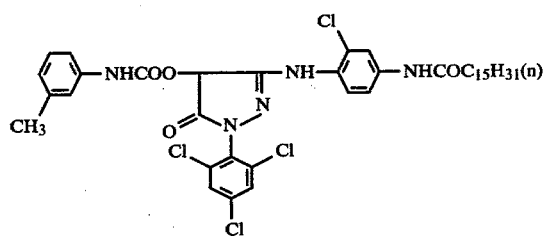

(14)
1-(2,4,6-trichlorophenyl)-3-{(2-chloro-4-n-hexadecanamido)anilino}-4-benzylaminocarbonyloxy-5-pyrazolone

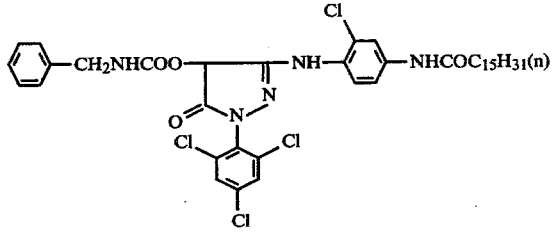

(15)
1-(2,4,6-trichlorophenyl)-3-{(2-chloro-4-n-hex-adecanamido)anilino}-4-ethylaminocarbonyloxy-5-pyrazolone

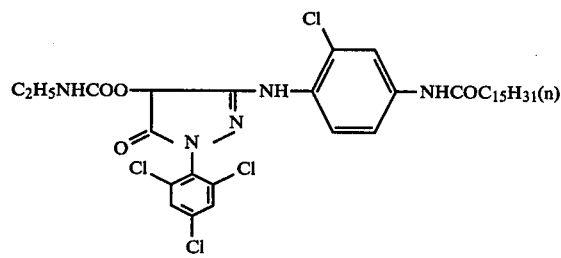

(17)
1-(2,4,6-trichlorophenyl)-3-{(2-chloro-5-octadecenyl-succinimido)anilino}-4-(α-naphthylaminocarbonylox-y)-5-pyrazolone

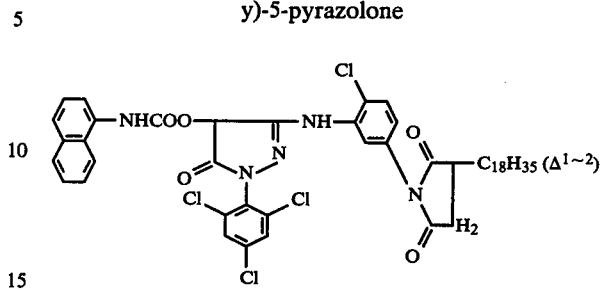

(16)
1-(2,4,6-trichlorophenyl)-3-{(2-chloro-5-octadecenyl-succinimido)amilino}-4-anilinocarbonyloxy-5-pyrazolone

(18)
1-(2,4,6-trichlorophenyl)-3-{(2-chloro-5-octadecenyl-succinimido)anilino}-4-(4-nitroanilino-carbonyloxy)-5-pyrazolone

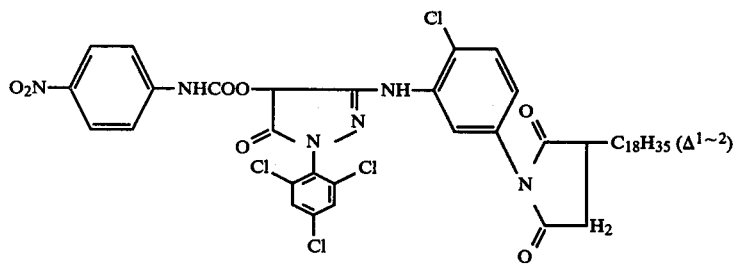

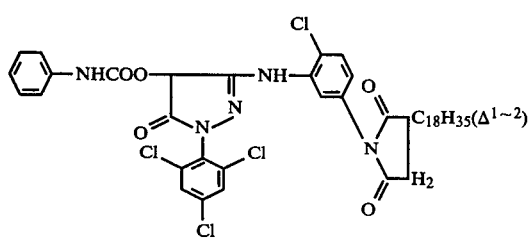

(19)
1-(2,4,6-trichlorophenyl)-3-{(2-chloro-5-octadecenyl-succinimido)anilino}-4-(4-chloroanilino-carbonyloxy)-5-pyrazolone

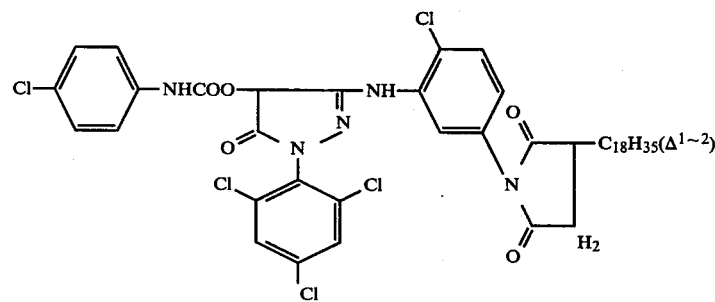

(20)

1-(2,4,6-trichlorophenyl)-3-{(2-chloro-5-dodecylsuccinimido)anilino}-4-ethylaminocarbonyloxy-5-pyrazolone

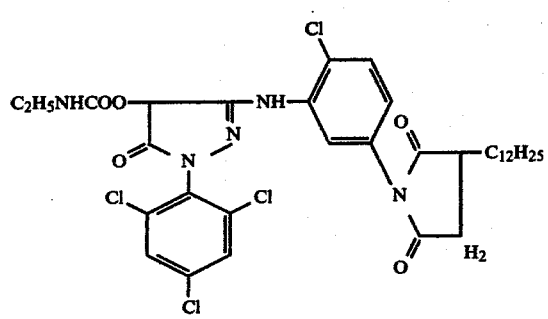

(21)

1-(2,4,6-trichlorophenyl)-3-{(2-chloro-5-n-dodecylcarbamoyl)anilino}-4-anilinocarbonyloxy-5-pyrazolone

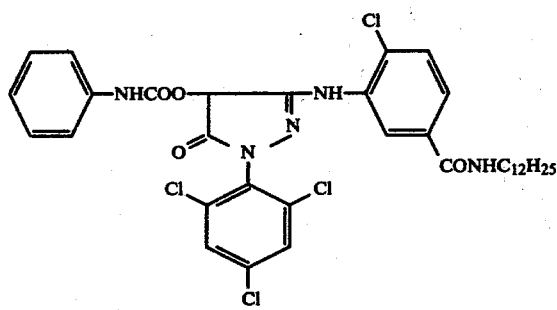

(22)

1-(2,4,6-trichlorophenyl)-3-{(2-methoxy-5-n-dodecylcarbamoyl)anilino}-4-(α-naphthylaminocarbonyloxy)-5-pyrazolone

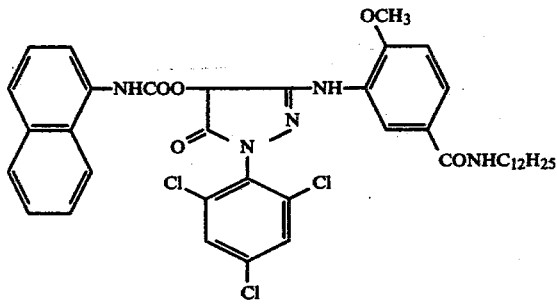

(23)

1-(2,4,6-trichlorophenyl)-3-{(2-chloro-5-n-dodecylcarbamoyl)anilino}-4-(4-nitroanilinocarbonyloxy)-5-pyrazolone

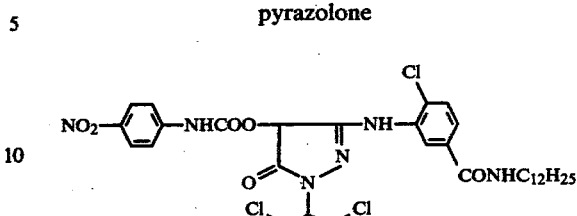

(24)

1-(2,4,6-trichlorophenyl)-3-{(2-chloro-5-n-dodecylcarbamoyl)anilino}-4-(4-chloroanilinocarbonyloxy)-5-pyrazolone

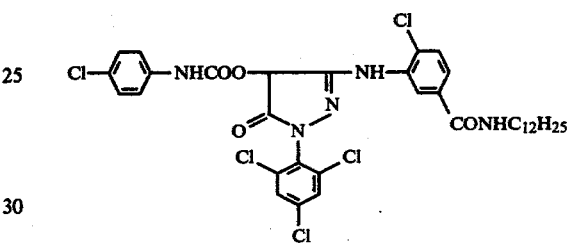

(25)

1-(2,4,6-trichlorophenyl)-3-{(2-chloro-5-n-dodecylcarbamoyl)anilino}-4-ethylaminocarbonyloxy-5-pyrazolone

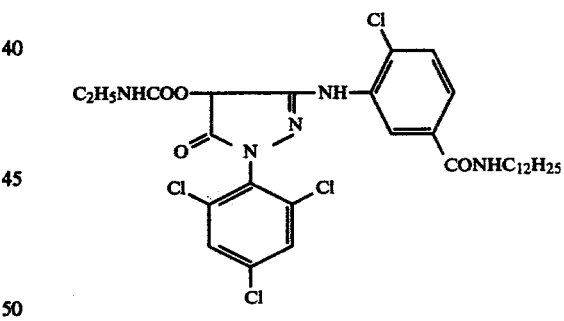

(26)

1-(2,4,6-trichlorophenyl)-3-{(2-chloro-5-n-dodecyloxycarbonyl)anilino}-4-anilinocarbonyloxy-5-pyrazolone

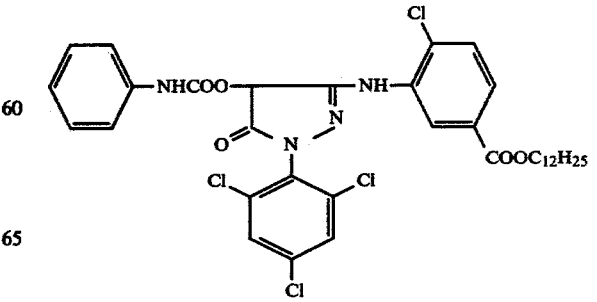

(27)
1-(2,4,6-trichlorophenyl)-3-{(2-chloro-5-n-dodecyloxycarbonyl)anilino}-4-ethylaminocarbonyloxy-5-pyrazolone

(28)
1-(2,4,6-trichlorophenyl)-3-[2-chloro-5-{γ-(2,4-di-t-amylphenoxy)propylsulfamoyl}anilino]-4-anilinocarbonyloxy-5-pyrazolone

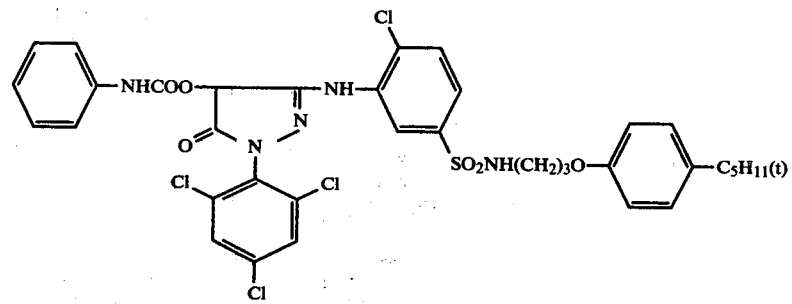

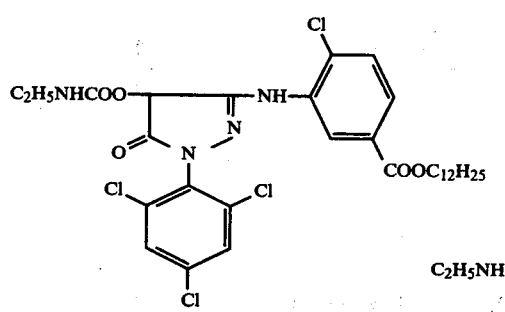

(29)
1-(2,4,6-trichlorophenyl)-3-[2-chloro-5-{γ-(2,4-di-t-amylphenoxy)propylsulfamoyl}anilino]-4-ethylaminocarbonyloxy-5-pyrazolone

(30)
1-(2,6-dichloro-4-methoxyphenyl)-3-[3-{α-(2,4-di-t-amylphenoxy)butanamido}benzamido]-4-(N-phenyl-N-acetylaminocarbonyloxy)-5-pyrazolone

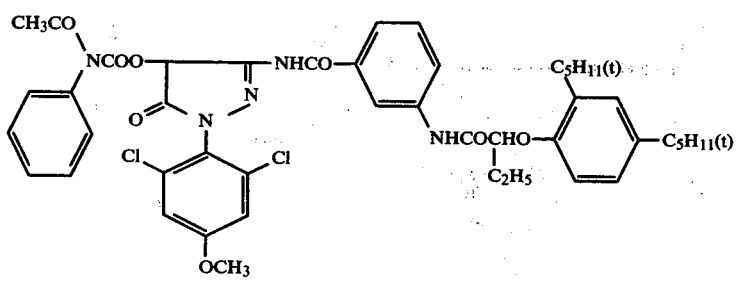

(31)
1-(2,6-dichloro-4-methoxyphenyl)-3-[3-{α-(2,4-di-t-amylphenoxy)butanamido}benzamido]-4-propylaminocarbonyloxy-5-pyrazolone

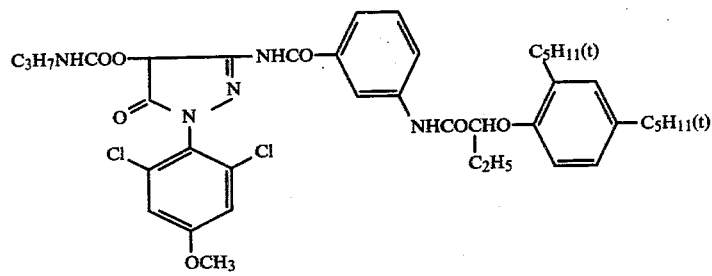

(32)
4,4'-(ethylenebisaminocarbonyloxy)bis-1-(2,4,6-trichlorophenyl)-3-[3-{α-(2,4-di-t-amylphenoxy)acetamido}benzamido]-5-pyrazolone

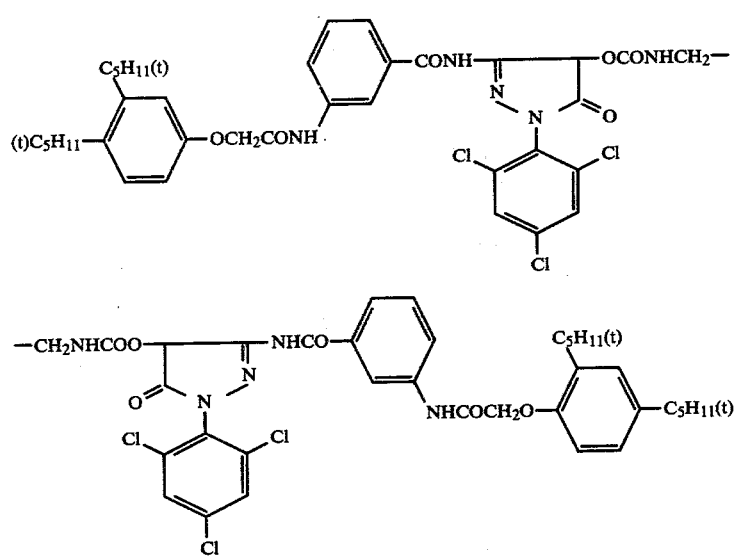

(33)
2-heptadecyl-3-(2,4-dichloroanilinocarbonyloxy)-pyrazolo[1,5-a]benzimidazol

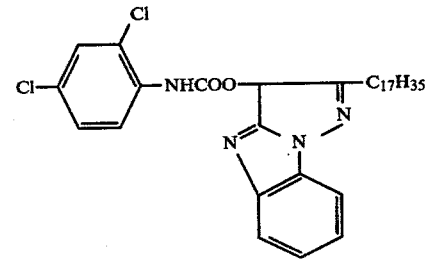

(34)
2-(2-chloroanilino)-3-(4-chloroanilinocarbonyloxy)-6-tridecanamido-pyrazolo[1,5-a]benzimidazol

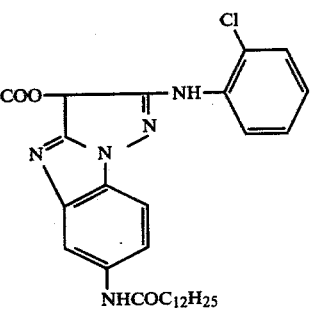

(35)
2-tetradecanamido-3-(4-cyanoanilinocarbonyloxy)-7-chloro-pyrazolo[1,5-a]benzimidazol

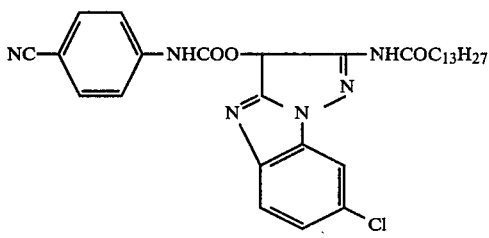

(36)
1-(2,6-dichloro-4-methoxyphenyl)-3-[3-{α-(2,4-di-t-amylphenoxy)butanamido}phenylureido]-4-(4-chloroanilinocarbonyloxy)-5-pyrazolone

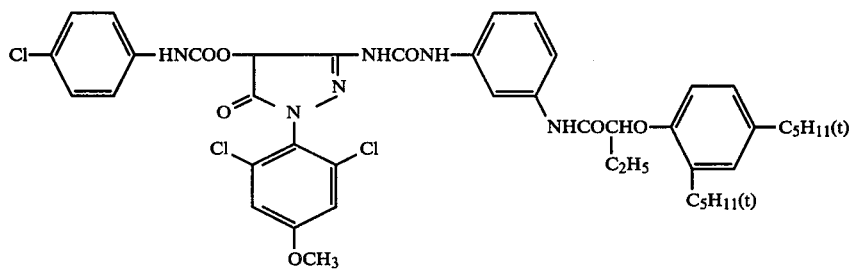

The couplers with substituted active points of the present invention represented by the foregoing general formulas (I), (II) or (III) can be synthesized for example by boiling under reflux 4-hydroxy-5-pyrazolones represented by the following general formula (VI):

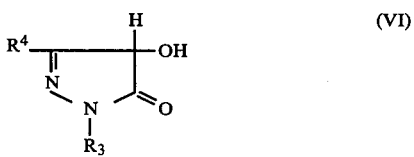

wherein $R_3$ and $R_4$ respectively have the same meaning as $R_3$ and $R_4$ in the foregoing general formula (IV), with a suitable amount of corresponding isocyanates in a sufficiently dired solvent such as toluene, xylene, dioxane or benzene thereby obtaining couplers which is substituted with an aminocarbonyloxy radical in the 4-position thereof.

The 4-hydroxy-5-pyrazolones represented by the formula (VI) can be obtained with a good yield by reducing corresponding pyrazolo-4,5-diones by means of an ordinary method for example catalytic reduction with a metallic catalyst such as paradium-carbon or reduction with zinc-acetic acid.

Further, said pyrazolo-4,5-diones can be easily obtained by conversion of 5-pyrazolone into corresponding azomethyne dye followed by hydrolysis with sulfuric acid as disclosed in U.S. Pat. No. 3,311,476 or by conversion of 5-pyrazolone into 4-aminopyrazolone followed by oxidation of amino radical as disclosed in U.S. Pat. No. 3,419,391.

Furthermore the synthesis of corresponding isocyanates is already well known, and certain isocyanates are easily commercially available.

In the following there is shown examples of synthesis of representative couplers of the present invention.

Synthesis Example 1 (synthesis of coupler No. 1)

0.01 mole of 1-(2,4,6-trichlorophenyl)-3-[3-{α-(2,4-di-t-amylphenoxy)acetamido}benzamido]-4-hydroxy-5-pyrazolone and 0.01 mole of phenyl isocyanate are dissolved in 100 ml of dehydrated toluene, added with 0.02 moles of pyridine and heated for 5 to 6 hours under reflux. The solvent is eliminated under reduced pressure after the reaction, and n-hexane is added. The solid is collected by filtration, then washed with n-hexane and dried to obtain the coupler (1) in a state of colorless powder with a melting point 72°-77° C.

Synthesis Example 2 (synthesis of coupler No. 3)

0.01 moles of 1-(2,4,6-trichlorophenyl)-3-[3-{α-(2,4-di-t-amylphenoxy)acetamido}benzamido]-hydroxy-5-pyrazolone and 0.01 moles of p-nitrophenyl isocyanate are dissolved in 100 ml of dehydrated toluene, then added with 0.02 moles of pyridine and heated for 1 to 1.5 hours under reflux. After the reaction the solvent is eliminated under reduced pressure and n-hexane is added. The obtained solid is collected by filtration, then washed with n-hexane and dried to obtain the coupler (3) in a state of colorless powder with a melting point of 96°-100° C.

Synthesis Example 3 (synthesis of coupler No. 9)

0.01 moles of 1-(2,4,6-trichlorophenyl)-3-{(2-chloro-4-n-hexadecanamido)anilino}-4-hydroxy-5-pyrazolone and 0.01 moles of phenyl isocyanate are dissolved in 100 ml of dehydrated toluene, then added with 0.02 moles of pyridine and heated for 1 to 1.5 hours under reflux. After the reaction the solvent is eliminated under reduced pressure, and n-hexane is added. The obtained solid is collected by filtration, and dried to obtain the coupler (9) in a state of colorless powder with a melting point of 85°-89° C.

Synthesis Example 4 (synthesis of coupler No. 11)

0.01 moles of 1-(2,4,6-trichlorophenyl)-3-{2-chloro-4-n-hexadecanamido)anilino}-4-hydroxy-5-pyrazolone and 0.01 moles of p-nitrophenyl isocyanate are dissolved in 100 ml of dehydrated toluene, then added with 0.02 moles of pyridine and heated for 1 to 1.5 hours under reflux. After the reaction the solvent is eliminated by distillation, and n-hexane is added. The obtained solid is collected by filtration and dried to obtain the coupler (II) in a state of colorless powder with a melting point of 106°-110° C.

Synthesis Example 5 (synthesis of coupler No. 18)

0.01 moles of 1-(2,4,6-trichlorophenyl)-3-{(2-chloro-5-octadecenylsuccinimido)anilino}-4-hydroxy-5-pyrazolone and 0.01 moles of p-nitrophenyl isocyanate are dissolved in 100 ml of dehydrated toluene, then added with 0.02 moles of triethyl amine and heated for 1 to 1.5 hours under reflux. After the reaction the solvent is distilled off and n-hexane is added. The obtained solid is collected by filtration and dried to obtain the coupler (18) in a state of colorless powder with a melting point of 118°–121° C.

The synthetic methods shown in the foregoing examples are applicable to various couplers, among which those listed before showed following results in the elementary analysis:

| Coupler | Elementary analysis (%) | | | | | | | | | |
|---|---|---|---|---|---|---|---|---|---|---|
| | Calculated value | | | | | Observed value | | | | |
| | C | H | N | Cl | S | C | H | N | Cl | S |
| (1) | 61.01 | 5.25 | 8.68 | 13.18 | — | 61.05 | 5.10 | 8.45 | 13.15 | — |
| (2) | 63.05 | 5.17 | 8.17 | 12.41 | — | 63.00 | 5.11 | 8.01 | 12.39 | — |
| (3) | 57.79 | 4.85 | 9.86 | 12.48 | — | 57.60 | 4.55 | 9.52 | 12.35 | — |
| (4) | 58.51 | 4.91 | 8.32 | 16.85 | — | 58.55 | 4.85 | 8.17 | 16.58 | — |
| (5) | 61.43 | 5.40 | 8.53 | 12.95 | — | 61.41 | 5.42 | 8.41 | 12.87 | — |
| (6) | 61.43 | 5.40 | 8.53 | 12.95 | — | 61.43 | 5.38 | 8.44 | 12.89 | — |
| (7) | 67.67 | 7.65 | 8.58 | 4.34 | — | 67.57 | 7.56 | 8.62 | 4.37 | — |
| (8) | 59.52 | 4.75 | 8.68 | 13.18 | — | 59.50 | 4.65 | 8.71 | 13.20 | — |
| (9) | 58.05 | 5.92 | 9.15 | 18.52 | — | 58.11 | 5.86 | 9.04 | 18.48 | — |
| (10) | 60.95 | 5.72 | 8.46 | 17.13 | — | 60.68 | 5.51 | 8.51 | 17.21 | — |
| (11) | 55.48 | 5.39 | 10.22 | 17.24 | — | 55.15 | 5.35 | 10.03 | 17.16 | — |
| (12) | 56.21 | 5.46 | 8.63 | 21.83 | — | 56.18 | 5.31 | 8.57 | 21.90 | — |
| (13) | 59.17 | 5.99 | 8.85 | 17.91 | — | 59.21 | 5.82 | 8.76 | 17.86 | — |
| (14) | 58.54 | 6.08 | 8.98 | 18.19 | — | 58.45 | 6.12 | 8.78 | 18.20 | — |
| (15) | 55.97 | 6.22 | 9.60 | 19.44 | — | 55.99 | 6.25 | 9.50 | 19.35 | — |
| (16) | 60.62 | 5.90 | 8.03 | 16.27 | — | 60.71 | 5.98 | 8.00 | 16.32 | — |
| (17) | 62.54 | 5.80 | 7.60 | 15.38 | — | 62.53 | 5.74 | 7.52 | 15.71 | — |
| (18) | 57.65 | 5.50 | 9.17 | 15.47 | — | 57.55 | 5.63 | 9.23 | 15.35 | — |
| (19) | 58.32 | 5.56 | 7.73 | 19.56 | — | 58.38 | 5.60 | 7.94 | 19.27 | — |
| (20) | 55.07 | 5.57 | 9.45 | 19.12 | — | 55.27 | 5.57 | 9.53 | 19.26 | — |
| (21) | 57.15 | 5.34 | 9.52 | 19.28 | — | 57.13 | 5.22 | 9.46 | 19.47 | — |
| (22) | 61.50 | 5.68 | 8.97 | 13.61 | — | 61.59 | 5.46 | 8.88 | 13.59 | — |
| (23) | 53.86 | 4.91 | 10.77 | 18.17 | — | 53.98 | 4.83 | 10.57 | 18.07 | — |
| (24) | 53.81 | 5.18 | 9.23 | 23.35 | — | 53.95 | 5.34 | 9.00 | 23.01 | — |
| (25) | 54.16 | 5.72 | 10.19 | 20.63 | — | 54.01 | 5.70 | 10.20 | 20.75 | — |
| (26) | 57.08 | 5.20 | 7.61 | 19.25 | — | 57.10 | 5.22 | 7.51 | 19.14 | — |
| (27) | 54.08 | 5.56 | 8.14 | 20.60 | — | 54.21 | 5.50 | 8.03 | 20.52 | — |
| (28) | 56.11 | 5.17 | 7.98 | 16.16 | 3.65 | 56.23 | 5.15 | 7.88 | 16.14 | 3.53 |
| (29) | 53.56 | 5.47 | 8.44 | 17.09 | 3.86 | 53.55 | 5.44 | 8.34 | 17.02 | 3.54 |
| (30) | 63.30 | 5.89 | 8.02 | 8.12 | — | 63.22 | 5.75 | 8.03 | 8.24 | — |
| (31) | 61.80 | 6.45 | 8.79 | 8.90 | — | 61.45 | 6.23 | 8.89 | 8.95 | — |
| (32) | 58.11 | 5.28 | 9.41 | 14.29 | — | 58.18 | 5.27 | 9.35 | 14.50 | — |
| (33) | 66.10 | 7.40 | 9.34 | 11.82 | — | 66.40 | 7.50 | 9.25 | 11.46 | — |
| (34) | 68.07 | 7.34 | 14.18 | 7.17 | — | 68.01 | 7.35 | 14.41 | 7.00 | — |
| (35) | 64.52 | 6.46 | 14.56 | 6.14 | — | 64.51 | 6.34 | 14.45 | 6.20 | — |
| (36) | 60.04 | 5.61 | 9.55 | 12.08 | — | 60.18 | 5.41 | 9.68 | 12.03 | — |

The couplers of the present invention thus obtained are provided, as explained before, with a significantly faster dye forming speed in the color development, which is not only faster than that of 4-equivalent couplers but also faster than that of 2-equivalent couplers wherein the split-off radical is an aryloxy radical such as phenoxy or nitrophenoxy radical or wherein the split-off radical such as acetoxy or benzoyloxy radical is connected by an ester bond. Besides the couplers of the present invention, even in comparison with conventional couplers of similar structure, are more easily dispersible in photographic protective colloid such as gelatin, and, in case of oil-soluble couplers, show excellent solubility in coupler solvent.

Based on these properties, the couplers of the present invention, when incorporated in the photographic sensitized layer as the internal type coupler, enable to reduce the thickness of photosensitive layer, to improve the sharpness etc. of the obtained color image, to prevent the loss of color density by undesirable gas such as formalin, and are free from undesirable effect on the developed color image. Furthermore said couplers are advantageous in the reduced color stain.

Thus the couplers of the present invention can have a wide range of application according to the various combination of the principal structure and the split-off radical, and are usable as diffusible couplers in case the magenta coupler residue is diffusible by the presence of water-soluble radical such as sulfonic or carboxylic radical and the split-off radical provided with the bonding radical according to the present invention is also diffusible, said diffusible couplers being adapted for use in the color developing solution for so-called external type photography.

Besides, in case the magenta coupler residue is diffusible while the split-off radical is non-diffusible due for example to the presence of an anti-diffusive radical such as long-chain aliphatic hydrocarbon residue such as octadecyl radical, the coupler composed of such coupler residue and such split-off radical is also usable in the external type photography in the same manner as explained above if said non-diffusive character is modest enough to render the entire structure of the coupler diffusible.

As already known, the external type photography consists of developing a light-sensitive material not containing coupler, particularly black-and-white silver halide light-sensitive photographic material specifically designed for this purpose with a color developing solution containing a coupler after exposure to cause penetration of a color developer and said coupler into said photographic material thereby causing a reaction between said color developer and diffusible coupler in the presence of silver halide having a developable nucleus and thus obtaining a dye image, and multi-colored image is generally obtained by successive developments with color developing solutions containing different couplers for example cyan, magenta and yellow couplers.

Such color developing solution may contain, in addition to aforementioned color developer and coupler, various components ordinarily employed in the color developing composition such as alkali sulfite, carbonate, bisulfite, bromide, iodide etc. A representative composition of such developing solution is as follows:

| Color developing solution | |
|---|---|
| Color developer | 1–5 g |
| Anhydrous sodium sulfite | 1–3 g |
| Anhydrous sodium carbonate | 10–60 g |
| Potassium bromide | 0.5–1.5 g |
| Coupler | 1–3 g |
| Water | to make 1 liter |

In case the couplers of the present invention is to be contained the external color developing solution, the couplers of the type particularly suitable for external development process as explained above are more easily soluble than the conventional couplers into the developing solution and are besides provided with aforementioned advantageous properties.

On the other hand the non-diffusible couplers wherein the magenta coupler residue and the split-off radical are both diffusible, or the non-diffusible couplers wherein the magenta coupler residue is non-diffusible but the split-off radical is diffusible, or the diffusible couplers wherein the magenta coupler residue is non-diffusible but the split-off radical is diffusible are adapted for use in the diffusion transfer process. The respective radical can be rendered diffusible by selecting a radical of a low molecular weight and/or introducing a water-soluble radical such as sulfonic radical, and can be rendered non-diffusible by introducing a long-chain aliphatic hydrocarbon residue and/or selecting a radical of relatively high molecular weight.

Further applicable to the diffusion transfer process are the couplers in which the magenta coupler residue and the split-off radical are both diffusible so long as the chemical species not required for the image formation at the color development are non-diffusible, such couplers being obtainable by introducing a hydroquinone or resorcin residue into the magenta coupler residue or split-off radical with or without a suitable bonding radical. Such combination of diffusibity of the magenta coupler residue and split-off radical is also applicable to the couplers of other types. The couplers known as so-called internal couplers which are incorporated in the photosensitive material particularly silver halide photosensitive material are preferably non-diffusible in order to prevent the effect on other layers, and the non-diffusible couplers previously cited as adapted for diffusion transfer process are also effective for this purpose. In such couplers the magenta coupler residue is preferably non-diffusible while the split-off radical may be either diffusible or non-diffusible.

Such internal couplers can be classified, according to the presence of hydrophilic or oleophilic radical in the molecule thereof, into so-called Fischer dispersion type couplers which are to be incorporated in the coating composition for the photosensitive layer as an alkaline solution and so-called protect type couplers which are to be incorporated as a solution in a coupler solvent.

The couplers of the present invention exhibit a superior solubility in comparison with the conventional couplers in the various dispersion methods as explained above according to various applications, thus resulting in various advantages such as color image of higher density, superior transparency of layer or improved resolution.

The couplers of the present invention, when incorporated in the photosensitive materials, are employed generally in an amount of approximately 0.07 to 0.7 moles, preferably 0.1 to 0.4 moles with respect to 1 mole of silver halide, or in an amount of approximately 0.01 to 0.1 moles preferably approximately 0.03 to 0.07 moles in case said coupler are used for the purpose of color correction by masking or of improving the characteristics of other couplers.

As thus far explained the couplers of the present invention are applicable in various manners according to respective purposes and exhibit excellent characteristics therein.

The photosensitive materials to which the couplers of the present invention are applied are preferably silver halide photosensitive materials of various types, for example silver halide photosensitive materials for diffusion transfer process as explained before, ordinary negative photosensitive materials, ordinary reversal photosensitive material, ordinary positive photosensitive materials, direct positive photosensitive materials, or special silver halide photosensitive materials such as for graphic arts, radiography, high resolution, infrared and ultraviolet photography.

Silver halide employed in such silver halide photosensitive materials is silver chloride, silver iodide, silver iodobromide, silver chlorobromide, silver chloroiodobromide etc. which can be prepared by neutral method, ammonia method etc. in various production process such as simultaneous mixing method or conversion method. In case of silver mixed halides, the mixing ratio thereof can be suitably chosen so as that the content of silver chloride becomes higher in a photosensitive material of relatively low sensitivity and of fine grain and lower in a material of relatively high sensitivity. Also the silver halides employed in the direct positive materials, which may be Harshel reversal type or solarization type, are generally provided previously with suitable fogging optically or chemically. Further, such various silver halides can be sensitized chemically by means for example of active gelatin; sulfur sensitizers such as allylthiocarbamide, thiourea or cystine; selenium sensitizers; reductive sensitizers such as stannous chloride or polyamines; precious metal sensitizers for example gold sensitizers such as potassium aurithiocyanate, potassium chloroaurate, 2-aurosulfobenzothioazole methyl chloride etc. or water-soluble salts of ruthenium, rhosium or iridium such as ammonium chloroparadate, potassium chloroplatinate or sodium chloroparadide (certain members of such compounds work as sensitizer or fog suppressor according the amount thereof), of suitable combinations thereof for example a combination of a gold sensitizer and a sulfur sensitizer or of a gold sensitizer and a selenium sensitizer.

Furthermore such silver halides can be spectrally sensitized in the desirable wavelength range by means for example of cyanine dyes such as zeromethyne, monomethyne, dimethyne or trimethyne dyes, or melocyanine dyes, or suitable combinations thereof such as super spectral sensitization.

Such silver halides are dispersed in suitable protective colloid to compose a photosensitive layer, and such protective colloid to be employed in said photosensitive layer or in other constituent layers such as intermediate layer, protective layer, filter layer, image receiving layer or a pH control layer placed for example under said image receiving layer is generally gelatin but can also be colloidal alubumin, cellulose derivatives or synthetic materials for example polyvinyl compounds such as polyvinyl alcohol, or further various combinations thereof. In addition acetyl cellulose with an acetyl content of 19–26%, water-soluble ethanolamine cellulose acetate etc. can be employed in combination with the above-mentioned materials.

The substrate of photosensitive materials can be composed of paper, laminated paper for example a laminate of polyethylene and paper, glass, cellulose acetate, cellulose nitrate, polyesters, polycarbonates, polyamides, polystyrenes, polyolefins in film or sheet form, and such substrate can be subjected to various hydrophilic treatments such as saponification, corona discharge, subbing or setting in order to improve the adhesion to various component layers.

The photosensitive material is composed at least of a substrate and a photosensitive layer provided thereon but usually contains at least several different layers positioned suitably according to the purpose as explained above, and, in case of a color photosensitive material, may contain two or more photosensitive layers which are sensitized for different wavelength ranges and may contain couplers for developing different colors.

The couplers of the present invention, being capable of providing a magenta dye when the magenta coupler residue thereof is utilized, are used in a color photographic material in combination with 2-equivalent or 4-equivalent cyan couplers such as naphthols or phenols and yellow couplers provided with active methylene radical between two carbonyl radicals, and such couplers are contained, in case of internal development photographic material, in respective photosensitive layers of suitable photosensitive wavelength ranges. Also in case of a pseudo color photographic material the couplers of the present invention can be employed singly or in combination with similar magenta couplers, wherein the relation between the photosensitive wavelength range and the coupler in ordinary color photographic material is not necessarily satisfied.

Furthermore, a photosensitive layer for a certain wavelength range may be composed of two or more layers which may be respectively provided with different sensitivities and which may respectively contain a 2-equivalent and a 4-equivalent couplers giving a same color for the purpose of further improving the resolution or improving the sensitivity.

As already explained above the couplers of the present invention can be used in combination with other 2- or 4-equivalent couplers, and in such case said 2-equivalent couplers may be so-called colored couplers for example provided at the active point thereof with a split-off radical connected through an azo radical as bonding radical, or so-called D.I.R. couplers capable of releasing a color development inhibitor at the color development, provided for example with a split-off radical connected through a thio radical as bonding radical.

Furthermore the photographic materials can contain, in the photosensitive layer and/or other constituent layers such as intermediate layer, subbing layer, filter layer, protective layer or image receiving layer, various additional photographic substances for example stabilizers such as mercury compounds, triazoles, azaindenes, zinc or cadmium salts; sensitizers such as quaternary ammonium salts or polyethylene glycol; materials for improving properties of layers such as glycerine, dihydroxyalkanes, ethylene bisglycolic acid esters or polymer emulsions; hardeners such as formaldehyde, halogenated fatty acids, disulfonic acid chlorides, bisazilydine or ethyleneimines; wetting agents such as saponine, polyethyleneglycol lauryl or oleyl ether, or sulfonated or alkylated polyethylene glycolates; organic solvents such as coupler solvents which are high-boiling and/or low-boiling organic solvents such as dibutyl phthalate, methanol, ethanol or ethylene cellosolve; so-called D.I.R. compounds capable of releasing a color development inhibitor and simultaneously forming a substantially colorless compound at the color development; antistatic agents; antifoaming agents; ultraviolet absorbants; fluorescent whiteners; antislipping agents; matting agents; antihalation and anti-irradiation agents singly or in combinations thereof.

Also an image receiving material which is separate from the photosensitive material but is used in combination therewith in diffusion transfer photographic process contains, on a photographic substrate as explained above, at least an image receiving layer and eventually a protective layer, subbing layer, pH control layer etc., which layers are composed of a protective colloid as aforementioned and may contain the additional photographic substances as aforementioned according to the purpose. For example the image receiving layer preferably contains compounds capable of capturing the dyes or dissipating the diffusibility thereof in order to prevent the rediffusion of diffusible dyes received from the photosensitive layer upon color development or to prevent the spreading of color. Also such compounds may be contained in a layer adjacent to said image receiving layer. Such compounds are exemplified by mordants such as polymers of aminoguanidine derivatives of vinylmethylketone as disclosed in the U.S. Pat. No. 2,882,156 or the mordant disclosed in the U.S. Pat. No. 3,271,148, or pH control agents such as inorganic or organic acids.

The color developing solution utilized for color development of photosensitive material after exposure thereof contains, as the principal component thereof, color developers which are exemplified by p-phenylenediamine derivatives such as diethyl-p-phenylene diamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)-toluene, N-ethyl-N-β-methane sulfonamidethyl-3-methyl-4-aminoaniline sulfurate, N-ethyl-N-β-methane sulfonamidethyl-4-aminoaniline, or 4-N-ethyl-N-β-hydroxyethylaminoaniline.

Such color developers may be used singly or in mutual combinations thereof, or, if desirable, in combination with black-and-white developers such as hydroquinone. Further the color developing solution generally contains alkaline materials such as sodium hydroxide, ammonium hydroxide, sodium carbonate, sodium sulfate or sodium sulfite, and may further contain additional substances for example alkali halides such as potassium bromide or development control agents such as cytrazinic acid. Such color development solution is previously contained in the image receiving material in a certain diffusion transfer process, and in such case it is also possible to add either one of the color developer and alkaline material in the image receiving material and effecting the development with a solution of the other component.

The couplers of the present invention react with the oxidation product generated at the development of silver halide with such color developer thereby forming a magenta dye, and also other dyes (including magenta dye) in case of certain couplers.

The removal of silver halide or developed silver from the photosensitive material after such color development is realized generally by a fixing solution, a combination of a fixing solution and a bleaching solution or a bleach-fixing solution which are employed in combination with related steps such as rinsing, stop-bath, stabilizing etc., wherein the fixing function is realized by dissolving materials for silver halides such as sodium thiosulfate or ammonium thiosulfate while the bleaching function is realized potassium ferricyanate or ferriammonium salt or sodium salt of ethylenediaminetetraacetic acid.

As thus far explained the couplers of the present invention are provided with superior characteristics for photographic use in comparison with conventional 2-equivalent couplers.

The present invention will be further clarified by the following example, which however will by no means limit the scope of the present invention:

EXAMPLE

The magenta couplers listed in the following Tab.1, wherein the couplers (1')–(22') and (33') are 4-equivalent couplers respectively obtained by substituting the active point substituent in the couplers (1)–(22) and (33) with a hydrogen atom, were respectively added in a mixture of 20 ml of dibutyl phthalate and 60 ml of ethyl acetate and completely dissolved by heating at 60° C. Each of thus obtained solutions was mixed with 10 ml of 6% aqueous solution of Alkanol B (alkylnaphthalene sulfonate produced by Du Pont de Nemeurs) and 200 ml of 6% aqueous solution of gelatin and emulsified therein by a colloid mill. Each coupler dispersion thus obtained was added to 1 kg of a high sensitivity silver iodobromide emulsion and coated on a film base to obtain a photographic sensitized material with a stable coated layer.

Said photographic sensitized material was developed, after exposure in an ordinary method, with Flexicolor Chemicals which is a color development kit supplied by Eastman Kodak Co. The characteristics of obtained magenta image are shown in Tab.1.

The aldehyde resistance values were determined by the following process. An exposed sample by a sensitometer and an unexposed sample were maintained in a closed container of relative humidity 75%, temperature 40° C. formaldehyde gas concentration $5 \times 10^{-4}$ mole/l, for 17 hours, then subjected to color development and the color density of the exposed sample was measured.

On the other hand, from the samples which were subjected color development without the formaldehyde treatment, the color density was measured.

The percentage of density loss by the formaldehyde treatment was determined from the following equation:

$$\text{Density loss (\%)} = \frac{(D_B - D_T)}{D_B} \times 100$$

wherein $D_B$: color density of sample not treated with formaldehyde;

$D_T$: color density of sample treated with formaldehyde.

Table 1

| Coupler No. | Max. density (D-max) | Aldehyde resistance (density loss %) | Coupler No. | Max. density (D-max) | Aldehyde resistance (density loss %) |
|---|---|---|---|---|---|
| (1') | 1.85 | 57 | (12') | 2.27 | 43 |
| (1) | 2.02 | 23 | (12) | 2.62 | 16 |
| (2') | 1.85 | 57 | (13') | 2.27 | 43 |
| (2) | 2.03 | 24 | (13) | 2.43 | 16 |
| (3') | 1.85 | 57 | (14') | 2.27 | 43 |
| (3) | 2.24 | 21 | (14) | 2.50 | 19 |
| (4') | 1.85 | 57 | (15') | 2.27 | 43 |
| (4) | 2.20 | 22 | (15) | 2.60 | 18 |
| (5') | 1.85 | 57 | (16') | 2.29 | 41 |
| (5) | 2.01 | 20 | (16) | 2.45 | 17 |
| (6') | 1.85 | 57 | (17') | 2.29 | 41 |
| (6) | 2.08 | 19 | (17) | 2.47 | 19 |
| (7') | 1.85 | 57 | (18') | 2.29 | 41 |
| (7) | 2.18 | 21 | (18) | 2.64 | 16 |
| (8') | 1.85 | 57 | (19') | 2.29 | 41 |
| (8) | 1.90 | 23 | (19) | 2.60 | 15 |
| (9') | 2.27 | 43 | (20') | 2.29 | 41 |
| (9) | 2.45 | 18 | (20) | 2.60 | 14 |
| (10') | 2.27 | 43 | (21') | 2.46 | 42 |
| (10) | 2.43 | 19 | (21) | 2.52 | 17 |
| (11') | 2.27 | 43 | (22') | 2.46 | 42 |
| (11) | 2.67 | 17 | (22) | 2.63 | 18 |
|  |  |  | (33') | 1.55 | 45 |
|  |  |  | (33) | 1.75 | 26 |

As shown in Tab. 1, the magenta couplers of the present invention exhibit superior color developing property and improved formaldehyde resistance in comparison with respectively corresponding 4-equivalent magenta couplers and thus are capable of providing excellent color images.

What is claimed is:

1. A process for forming a photographic magenta dye image which comprises contacting exposed silver halide with a color developing agent in the presence of a 2-equivalent magenta coupler represented by the following formula:

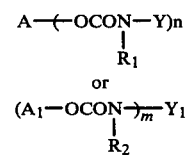

wherein $R_1$ and $R_2$ are individually hydrogen or a monovalent organic group selected from the class consisting of acyl and aliphatic hydrocarbon radicals which can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, and arylsulfonamido; Y is a monovalent organic radical selected from the class consisting of an aromatic hydrocarbon residue, an aliphatic hydrocarbon residue, a heterocyclic residue, acyl, thioalkyl, and —SO₂X wherein X is an aliphatic hydrocarbon residue, all of which can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, and arylsulfonamido, the heterocyclic residue being selected from the class consisting of pyridyl, quinolyl, furyl, benzothiazolyl, oxazolyl, imidazolyl, and naphthoxazolyl; Y₁ is an m-valent organic radical selected from the class consisting of m-valent residues of an aliphatic hydrocarbon residue, an aromatic hydrocarbon residue and a heterocyclic residue, all of said residues can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, and arylsulfonamido, the heterocyclic residue being selected from the group consisting of residues of pyridine, quinoline, furan, benzothiazoline, oxazoline, imidazoline and naphthoxazoline; and A and A₁ are respectively n-valent and monovalent residues of a magenta coupler which are represented by the following formula when the split-off groups

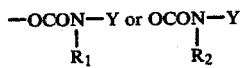

are removed from the magenta couplers:

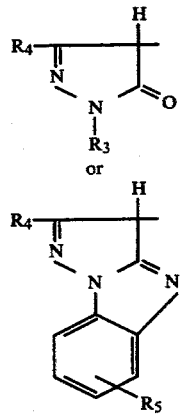

wherein R₃ is selected from the group consisting of hydrogen, alkenyl, alkyl, which contains up to 50 carbon atoms, a cycloalkyl group which can have at least one substituent selected from halogen, nitro, cyano, aryl, alkoxy, aryloxycarbonyl, alkoxycarbonyl, aryloxycarboxy, sulfo, sulfamoyl, carbamoyl, acylamino, ureido, heterocyclic, arylsulfonyloxy and oxo, aryl which can have at least one substituent selected from halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, a heterocyclic radical selected from the class consisting of pyridyl, quinolyl, furyl, benzothiazolyl, oxazolyl, imidazolyl and naphthoxazolyl wherein said radicals can have at least one substituent selected from the class consisting of halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, carbamoyl and thiocarbamoyl; R₄ is alkyl having up to 50 carbon atoms which can have at least one substituent selected from halogen, nitro, cyano, aryl, alkoxy, aryloxycarbonyl, alkoxycarbonyl, aryloxycarboxy, sulfo, sulfamoyl, carbamoyl, acylamino, ureido, heterocyclic, arylsulfonyloxy and oxo, aryl which can have at least one substituent selected from halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, a heterocyclic radical selected from the class consisting of pyridyl, quinolyl, furyl, benzothiazolyl, oxazolyl, imidazolyl and naphthoxazolyl wherein said radicals can have at least one substituent selected from the class consisting of halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, alkoxycarbonyl, aryloxycarbonyl, aralyloxycarbonyl, an alkylthio group, an arylthio group, an alkoxy group, an aryloxy group, an alkylthio group, an arylthio group, an amino group, a carboxy group, an amido radical, an N-alkylacylamino radical, an N-arylacylamino radical, an ureido radical, a thioureido radical, a quanidino radical a piperidino radical or a pyroridino radical; and R₅ is one to four monovalent radicals selected from a hydrogen atom, a halogen atom, an alkyl radical, an alkoxy radical, an amido radical, a carbamoyl radical and a sulfamoyl radical, and m and n are individually a positive integer.

2. The process for forming a photographic magenta dye image according to claim 1 wherein R₁ and R₂ are individually a hydrogen or an acyl radical which can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido and arylsulfonamido.

3. The process for forming a photographic magneta dye image according to claim 1 wherein Y is alkyl, alkenyl, aryl, a heterocyclic residue, acyl, thioacyl or —SO₂—X wherein X is alkyl or an alkenyl radical, all of which can have at least one substituent selected from the class consisting of halogen, nitro, cyano, aryl, alkoxy, aryloxycarboxy, aryloxycarbonyl, arylcarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido and arylsulfonamido, the heterocyclic residue being selected from the class consisting of pyridyl, quinolyl, furyl, benzothiazolyl, oxazolyl, imidazolyl and naphthoxazolyl.

4. The process for forming a photographic magenta dye image according to claim 1 wherein Y₁ is an m-valent organic radical selected from the class consisting of m-valent residues of an alkyl residue, an alkenyl residue, an aryl residue and a heterocyclic residue, said residues can have at least one subsitituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, arylsulfonamido, the heterocyclic residue being selected from the group consisting of residues of pyridine, quinoline, furan, benzothiazoline, oxazoline, imidazoline and naphthothiazoline, and oxygen, sulfur, amino sulfonyl, carbonyloxy, aminocarbonyl and sulfoamido.

5. The process for forming a photographic magenta dye image according to claim 1 wherein $R_3$ is an aryl radical which can have at least one substituent selected from a halogen atom and alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro radicals.

6. The process for forming a photographic magenta dye image according to claim 5 wherein $R_3$ is a phenyl radical of which at least one ortho position is substituted with an alkyl or alkoxy radical or a halogen atom.

7. The process for forming a photographic magenta dye image according to claim 1 wherein $R_4$ is alkyl which can have at least one substituent selected from halogen, nitro, cyano, aryl, alkoxy, aryloxycarbonyl, alkoxycarbonyl, aryloxycarboxy, sulfo, sulfamoyl, carbamoyl, acylamino, ureido, heterocyclic, arylsulfonyloxy and oxo, the alkyl group containing 1 to 50 carbon atoms, aryl which can have at least one substituent selected from halogen, alkyl, alkoxy, aryloxy carboxy, alkoxycarbonyl, acylamino, carbamoyl, alkylcarbamoyl, dialkylcarbamoyl, arylcarbamoyl, alkylsulfonamido, arylsulfonamido, cyano and nitro, a heterocyclic radical selected from the class consisting of pyridyl, quinolyl, furyl, benzothiazolyl, oxazolyl, imidazolyl and naphthoxazolyl which can have at least one substituent selected from the class consisting of halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, alkoxycarbonyl, aryloxycarbonyl, aralkyloxycarbonyl, methoxy, ethoxy, phenoxy, tolyloxy, ethylthio, propylthio, phenylthio, tolylthio, carboxy, N-alkylamino, cycloalkylamino, N,N-dialkylamino, N-alkyl-N-arylamino, N-arylamino, amido, N-alkylacylamino, N-arylacylamino, N-arylureido, N-alkylureido, N-alkylthioureido, N-arylthioureido, carbamoyl, N-alkylguanidino, N-arylguanidino or sulfamoyl.

8. The process for forming a photographic magenta dye image according to claim 1 wherein $R_5$ is one to four monovalent radicals selected from a hydrogen atom, a chlorine atom, a methyl radical, an ethyl radical, a methoxy radical, an ethoxy radical, an acetamido radical, a benzenesulfonamido radical, a 2,4-di-t-amylphenoxyacetamido radical, a dodecylcarbamoyl radical and a dodecylsulfamoyl radical.

9. The process for forming a photographic magenta dye image according to claim 1 wherein n and m are individually 1, 2 or 3.

10. The process for forming a photographic magenta dye image according to claim 7 wherein n and m are individually 1 or 2.

11. The light-sensitive silver halide photographic material having a support and coated thereon a light-sensitive silver halide emulsion layer containing a magenta coupler represented by the following general formulae:

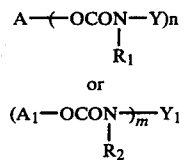

wherein $R_1$ and $R_2$ are individually hydrogen or a monovalent organic group selected from the class consisting of acyl and aliphatic hydrocarbon radicals which can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, and arylsulfonamido Y is a monovalent organic radical selected from the class consisting of an aromatic hydrocarbon residue, an aliphatic hydrocarbon residue, a heterocyclic residue, acyl, thioalkyl, and —SO$_2$X wherein X is an aliphatic hydrocarbon residue, all of which can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, and arylsulfonamido, the heterocyclic residue being selected from the class consisting of pyridyl, quinolyl, furyl, benzothiazolyl, oxazolyl, imidazolyl, and naphthoxazolyl; $Y_1$ is a m-valent organic radical selected from the class consisting of m-valent residues of an aliphatic hydrocarbon residue, an aromatic hydrocarbon residue and a heterocyclic residue, all of said residues can have at least one substituent selected from the class consisting of halogen, nitro, cyano, aryl, alkoxy, aryloxycarboxy, alkoxycarbonyl, aryloxycarbonyl, sulfo, sulfamoyl, carbamoyl, acylamino, ureido, arylsulfonyloxy, oxo, alkyl, aryloxy, carboxy, alkylcarbamoyl, arylcarbamoyl, alkylsulfonamido, and arylsulfonamido, the heterocyclic residue being selected from the group consisting of residues of pyridine, quinoline, furan, benzothiazoline, oxazoline, imidazoline and naphthoxazoline; and A and $A_1$ are respectively n-valent and monovalent residues of a magenta coupler which are represented by the following formula when the split-off group

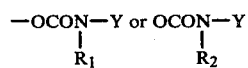

is removed from the magenta couplers:

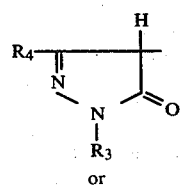

-continued $$\begin{array}{c} R_4-\overset{H}{\underset{N}{\parallel}}\diagdown\\ \phantom{xx}N\diagup\phantom{x}N\\ \end{array}\bigg\langle\begin{array}{c}\\ \\ R_5\end{array}$$

wherein R₃ is selected from the group consisting of hydrogen, alkenyl, alkyl which contains up to 50 carbon atoms a cycloalkyl group which can have at least one substituent selected from halogen, nitro, cyano, aryl, alkoxy, aryloxycarbonyl, aryloxycarboxy, alkoxycarbonyl, sulfo, sulfamoyl, carbamoyl, acylamino, ureido, heterocyclic, arylsulfonyloxy and oxo, aryl which can have at least one substituent selected from halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, a heterocyclic radical selected from the class consisting of pyridyl, quinolyl, furyl, benzothiazolyl, oxazolyl, imidazolyl and naphthoxazolyl wherein said radicals can have at least one substituent selected from the class consisting of halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, carbamoyl and thiocarbamoyl; R₄ is alkyl having up to 50 carbon atoms which can have at least one substituent selected from halogen, nitro, cyano, aryl, alkoxy, aryloxycarbonyl, alkoxycarbonyl, aryloxycarboxy, sulfo, sulfamoyl, carbamoyl, acylamino, ureido, heterocyclic, arylsulfonyloxy and oxo, aryl which can have at least one substituent selected from halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, a heterocyclic radical selected from the class consisting of pyridyl, quinolyl, furyl, benzothiazolyl, oxazolyl, imidazolyl and naphthoxazolyl wherein said radicals can have at least one substituent selected from the class consisting of halogen, alkyl, alkoxy, aryloxy, carboxy, alkoxycarbonyl, acylamino, carbamoyl, alkylcarbamoyl, dialkylcarbamoyl, arylcarbamoyl, alkylsulfonamido, arylsulfonamido, cyano and nitro, alkoxycarbonyl, aryloxycarbonyl, aralyloxycarbonyl, an alkylthio group, an arylthio group, an alkoxy group, an aryloxy group, an alkylthio group, an arylthio group, an amino group, a carboxy group, an amido radical, an N-alkylacylamino radical, an N-arylacylamino radical, an ureido radical, a thioureido radical, a guanidino radical, a piperidino radical or a pyroridino radical; and R₅ is one to four monovalent radicals selected from a hydrogen atom, a halogen atom, an alkyl radical, an alkoxy radical, an amido radical, a carbamoyl radical and a sulfamoyl radical, and m and n are individually a positive integer.

* * * * *

UNITED STATES PATENT AND TRADEMARK OFFICE
CERTIFICATE OF CORRECTION

PATENT NO. : 4,191,574
DATED : March 4, 1980.
INVENTOR(S) : ENDO, et al

It is certified that error appears in the above-identified patent and that said Letters Patent are hereby corrected as shown below:

In the Title Page, under Foreign Application Priority Data, correct to read as follows -- Feb. 21, 1975 [JP] Japan.........50/21687 --

Column 1, line 8, cancel "21607/1975 filed on Feb. 21, 1975" insert -- 21687/1975 filed on Feb. 21, 1975 --

Signed and Sealed this

Fifteenth Day of July 1980

[SEAL]

Attest:

SIDNEY A. DIAMOND

Attesting Officer

Commissioner of Patents and Trademarks